United States Patent
Wu

(10) Patent No.: US 10,345,255 B2
(45) Date of Patent: *Jul. 9, 2019

(54) RAPID-READ GATED AMPEROMETRY DEVICES

(71) Applicant: Bayer HealthCare LLC, Whippany, NJ (US)

(72) Inventor: Huan-Ping Wu, Granger, IN (US)

(73) Assignee: ASCENSIA DIABETES CARE HOLDINGS AG, Basel (CH)

( * ) Notice: Subject to any disclaimer, the term of this patent is extended or adjusted under 35 U.S.C. 154(b) by 484 days.

This patent is subject to a terminal disclaimer.

(21) Appl. No.: 14/688,055

(22) Filed: Apr. 16, 2015

(65) Prior Publication Data

US 2015/0219586 A1    Aug. 6, 2015

Related U.S. Application Data

(60) Continuation of application No. 13/401,222, filed on Feb. 21, 2012, now Pat. No. 9,034,160, which is a
(Continued)

(51) Int. Cl.
*G01N 27/327* (2006.01)
*G01N 27/406* (2006.01)
*G01N 35/00* (2006.01)

(52) U.S. Cl.
CPC ....... *G01N 27/327* (2013.01); *G01N 27/3273* (2013.01); *G01N 27/4065* (2013.01); *G01N 35/0092* (2013.01)

(58) Field of Classification Search
CPC ... G01N 27/327–3274; G01N 27/4065; G01N 35/0092; G01N 2035/0097; C12Q 1/00–006
See application file for complete search history.

(56) References Cited

U.S. PATENT DOCUMENTS 4,897,162 A    1/1990  Lewandowski
4,994,167 A    2/1991  Shults
(Continued)

FOREIGN PATENT DOCUMENTS

JP    2000180399    6/2000
JP    2001041925    2/2001
(Continued)

OTHER PUBLICATIONS

Gunasingham, et al., "Pulsed Amperometric Detection of Glucose Using a Mediated Enzyme Electrode", Journal of Electroanalytical Chemistry, vol. 287, No. 2, pp. 342-362, 1990.*
(Continued)

*Primary Examiner* — Maris R Kessel

(74) *Attorney, Agent, or Firm* — Nixon Peabody LLP

(57) ABSTRACT

A sensor system, device, and methods for determining the concentration of an analyte in a sample is described. Input signals including multiple duty cycles of sequential excitation pulses and relaxations are input to the sample. One or more signals output from the sample within 300 ms of the input of an excitation pulse may be correlated with the analyte concentration of the sample to improve the accuracy and/or precision of the analysis. Determining the analyte concentration of the sample from these rapidly measured output values may reduce analysis errors arising from the hematocrit effect, mediator background, and other error sources.

36 Claims, 4 Drawing Sheets

Related U.S. Application Data division of application No. 12/271,032, filed on Nov. 14, 2008, now Pat. No. 8,147,674.

(60) Provisional application No. 61/012,729, filed on Dec. 10, 2007.

(56) References Cited

U.S. PATENT DOCUMENTS

| | | |
|---|---|---|
| 5,120,420 A | 6/1992 | Nankai |
| 5,131,999 A | 7/1992 | Gunasingham |
| 5,620,579 A | 4/1997 | Genshaw |
| 5,653,863 A | 8/1997 | Genshaw |
| 5,708,247 A | 1/1998 | McAleer |
| 5,807,375 A | 9/1998 | Gross |
| 5,820,622 A | 10/1998 | Gross |
| 5,942,102 A | 8/1999 | Hodges |
| 5,951,836 A | 9/1999 | McAleer |
| 6,086,748 A | 7/2000 | Durst |
| 6,090,268 A | 7/2000 | Kunimatsu |
| 6,153,069 A | 11/2000 | Pottgen |
| 6,275,717 B1 | 8/2001 | Gross |
| 6,413,411 B1 | 7/2002 | Pottgen |
| 6,576,117 B1 | 6/2003 | Iketaki |
| 6,721,586 B2 | 4/2004 | Kiser |
| 6,824,670 B2 | 11/2004 | Tokunaga |
| 7,096,126 B2 | 8/2006 | Geutebrueck |
| 7,122,111 B2 | 10/2006 | Tokunaga |
| 7,351,323 B2 | 4/2008 | Iketaki |
| 7,468,125 B2 | 12/2008 | Kraft |
| 7,537,684 B2 | 5/2009 | Sato |
| 7,862,696 B2 | 1/2011 | Wu |
| 8,088,272 B2 | 1/2012 | Deng |
| 8,093,903 B2 | 1/2012 | Kraft |
| 8,101,062 B2 | 1/2012 | Deng |
| 8,105,478 B2 | 1/2012 | Barlag |
| 2002/0180446 A1 | 12/2002 | Kuhr |
| 2003/0113933 A1 | 6/2003 | Jansson |
| 2003/0178322 A1 | 9/2003 | Iyengar |
| 2004/0072158 A1 | 4/2004 | Henkens |
| 2005/0176153 A1 | 8/2005 | O'hara |
| 2007/0246357 A1 | 10/2007 | Wu |
| 2008/0173552 A1 | 7/2008 | Wu |
| 2008/0179197 A1 | 7/2008 | Wu |
| 2009/0068754 A1 | 3/2009 | Wu |

FOREIGN PATENT DOCUMENTS

| | | |
|---|---|---|
| JP | 2005147990 | 6/2005 |
| WO | WO 92/15955 A1 | 9/1992 |
| WO | WO 96/14026 | 5/1996 |
| WO | WO 01/57510 A2 | 8/2001 |
| WO | WO 2004/053476 A1 | 6/2004 |
| WO | WO 2005/114164 A2 | 12/2005 |
| WO | WO 2007/013915 A1 | 2/2007 |
| WO | WO 2007/133985 A2 | 11/2007 |
| WO | WO 2007/133985 A3 | 11/2007 |

OTHER PUBLICATIONS

Gunasingham, et al., "Pulsed Amperometric Detection of Glucose Using a Mediated Enzyme Electrode", Journal of Electroanalytical Chemistry, 1990, pp. 349-362, vol. 287, No. 2.

WIPO, "International Search Report for PCT/US2008/080865", Jan. 9, 2009, Publisher: International Searching Authority.

Extended European Search Report for Application No. EP 18176551.2, dated Sep. 28, 2018 (7 pages).

* cited by examiner

RAPID-READ GATED AMPEROMETRY DEVICES

CROSS REFERENCE TO RELATED APPLICATIONS

This application is a continuation of U.S. patent application Ser. No. 13/401,222, filed Feb. 21, 2012, now allowed, which is a division of U.S. Nonprovisional application Ser. No. 12/271,032, filed Nov. 14, 2008, now U.S. Pat. No. 8,147,674, entitled "Rapid Read Gated Amperometry", which claimed the benefit of U.S. Provisional Application No. 61/012,729 entitled "Rapid-Read Gated Amperometry" as filed on Dec. 10, 2007, all of which are incorporated herein by reference in their entireties.

BACKGROUND

Biosensors provide an analysis of a biological fluid, such as whole blood, serum, plasma, urine, saliva, interstitial, or intracellular fluid. Typically, biosensors have a measurement device that analyzes a sample residing in a sensor strip. The sample usually is in liquid form and in addition to being a biological fluid, may be the derivative of a biological fluid, such as an extract, a dilution, a filtrate, or a reconstituted precipitate. The analysis performed by the biosensor determines the presence and/or concentration of one or more analytes, such as alcohol, glucose, uric acid, lactate, cholesterol, bilirubin, free fatty acids, triglycerides, proteins, ketones, phenylalanine or enzymes, in the biological fluid. The analysis may be useful in the diagnosis and treatment of physiological abnormalities. For example, a diabetic individual may use a biosensor to determine the glucose level in whole blood for adjustments to diet and/or medication.

Biosensors may be designed to analyze one or more analytes and may use different sample volumes. Some biosensors may analyze a single drop of whole blood, such as from 0.25-15 microliters (μL) in volume. Biosensors may be implemented using bench-top, portable, and like measurement devices. Portable measurement devices may be hand-held and allow for the identification and/or quantification of one or more analytes in a sample. Examples of portable measurement devices include the Ascensia Breeze® and Elite® meters of Bayer HealthCare in Tarrytown, N.Y., while examples of bench-top measurement devices include the Electrochemical Workstation available from CH Instruments in Austin, Tex. Biosensors providing shorter analysis times, while supplying the desired accuracy and/or precision, provide a substantial benefit to the user.

Biosensors may use optical and/or electrochemical methods to analyze the sample. In some optical systems, the analyte concentration is determined by measuring light that has interacted with or been absorbed by a light-identifiable species, such as the analyte or a reaction or product formed from a chemical indicator reacting with the analyte. In other optical systems, a chemical indicator fluoresces or emits light in response to the analyte when illuminated by an excitation beam. The light may be converted into an electrical output signal, such as current or potential, which may be similarly processed to the output signal from an electrochemical method. In either optical system, the biosensor measures and correlates the light with the analyte concentration of the sample.

In electrochemical biosensors, the analyte concentration is determined from an electrical signal generated by an oxidation/reduction or redox reaction of the analyte or a species responsive to the analyte when an input signal is applied to the sample. The input signal may be applied as a single pulse or in multiple pulses, sequences, or cycles. An oxidoreductase, such as an enzyme or similar species, may be added to the sample to enhance the electron transfer from a first species to a second species during the redox reaction. The enzyme or similar species may react with a single analyte, thus providing specificity to a portion of the generated output signal. Examples of some specific oxidoreductases and corresponding analytes are given below in Table I.

TABLE I

| Oxidoreductase (reagent layer) | Analyte |
|---|---|
| Glucose dehydrogenase | β-glucose |
| Glucose oxidase | β-glucose |
| Cholesterol esterase; cholesterol oxidase | Cholesterol |
| Lipoprotein lipase; glycerol kinase; glycerol-3-phosphate oxidase | Triglycerides |
| Lactate oxidase; lactate dehydrogenase; diaphorase | Lactate |
| Pyruvate oxidase | Pyruvate |
| Alcohol oxidase | Alcohol |
| Bilirubin oxidase | Bilirubin |
| Uricase | Uric acid |
| Glutathione reductase | NAD(P)H |
| Carbon monoxide oxidoreductase | Carbon monoxide |

A mediator may be used to maintain the oxidation state of the enzyme. Table II, below, provides some conventional combinations of enzymes and mediators for use with specific analytes.

TABLE II

| Analyte | Enzyme | Mediator |
|---|---|---|
| Glucose | Glucose Oxidase | Ferricyanide |
| Glucose | Glucose Dehydrogenase | Ferricyanide |
| Cholesterol | Cholesterol Oxidase | Ferricyanide |
| Lactate | Lactate Oxidase | Ferricyanide |
| Uric Acid | Uricase | Ferricyanide |
| Alcohol | Alcohol Oxidase | Phenylenediamine |

Electrochemical biosensors usually include a measurement device having electrical contacts that connect with electrical conductors in the sensor strip. The conductors may be made from conductive materials, such as solid metals, metal pastes, conductive carbon, conductive carbon pastes, conductive polymers, and the like. The electrical conductors typically connect to working, counter, reference, and/or other electrodes that extend into a sample reservoir. One or more electrical conductors also may extend into the sample reservoir to provide functionality not provided by the electrodes.

In many biosensors, the sensor strip may be adapted for use outside, inside, or partially inside a living organism. When used outside a living organism, a sample of the biological fluid is introduced into a sample reservoir in the sensor strip. The sensor strip may be placed in the measurement device before, after, or during the introduction of the sample for analysis. When inside or partially inside a living organism, the sensor strip may be continually immersed in the sample or the sample may be intermittently introduced to the strip. The sensor strip may include a reservoir that partially isolates a volume of the sample or be open to the sample. Similarly, the sample may continuously flow through the strip or be interrupted for analysis.

The measurement device applies an input signal through the electrical contacts to the electrical conductors of the sensor strip. The electrical conductors convey the input signal through the electrodes into the sample present in the sample reservoir. The redox reaction of the analyte generates an electrical output signal in response to the input signal. The electrical output signal from the strip may be a current (as generated by amperometry or voltammetry), a potential (as generated by potentiometry/galvanometry), or an accumulated charge (as generated by coulometry). The measurement device may have the processing capability to measure and correlate the output signal with the presence and/or concentration of one or more analytes in the biological fluid.

In conventional amperometry, current is measured during a read pulse as a constant potential (voltage) is applied across the working and counter electrodes of the sensor strip. The measured current is used to quantify the analyte in the sample. Amperometry measures the rate at which an electrochemically active, thus measurable, species is being oxidized or reduced at or near the working electrode. Many variations of the amperometric method for biosensors have been described, for example in U.S. Pat. Nos. 5,620,579; 5,653,863; 6,153,069; and 6,413,411.

A disadvantage of conventional amperometric methods is the non-steady-state nature of the current after a potential is applied. The rate of current change with respect to time is very fast initially and becomes slower as the analysis proceeds due to the changing nature of the underlying diffusion process. Until the consumption rate of the ionized measurable species at the electrode surface equals the diffusion rate, a steady-state current cannot be obtained. Thus, conventional amperometry methods that measure the current during the transient period before a steady-state condition is reached, may provide more inaccuracy than if the measurement is taken during a steady-state time period.

The measurement performance of a biosensor is defined in terms of accuracy and/or precision. Increases in accuracy and/or precision provide for an increase in measurement performance for the biosensor. Accuracy may be expressed in terms of bias of the biosensor's analyte reading in comparison to a reference analyte reading, with larger bias values representing less accuracy, while precision may be expressed in terms of the spread or variance among multiple analyte readings in relation to a mean. Bias is the difference between a value determined from the biosensor and the accepted reference value and may be expressed in terms of "absolute bias" or "relative bias". Absolute bias may be expressed in the units of the measurement, such as mg/dL, while relative bias may be expressed as a percentage of the absolute bias value over the reference value. Reference values may be obtained with a reference instrument, such as the YSI 2300 STAT PLUS™ available from YSI Inc., Yellow Springs, Ohio.

Many biosensors include one or more methods to correct the error associated with an analysis. The concentration values obtained from an analysis with an error may be inaccurate. The ability to correct these inaccurate analyses may increase the accuracy of the concentration values obtained. An error correction system may compensate for one or more errors, such as sample hematocrit content, which is different from a reference sample. For example, conventional biosensors may be configured to report glucose concentrations presuming a 40% (v/v) hematocrit content for a whole blood sample, regardless of the actual hematocrit content of the sample. In these systems, any glucose measurement performed on a whole blood sample containing less or more than 40% hematocrit will include error or bias attributable to the "hematocrit effect".

In conventional biosensor sensor strips for determining glucose concentrations, glucose may be oxidized by an enzyme, which then transfers the electron to a mediator. This reduced mediator then travels to the working electrode where it is electrochemically oxidized. The amount of mediator being oxidized may be correlated to the current flowing between the working and counter electrodes of the sensor strip. Quantitatively, the current measured at the working electrode is directly proportional to the diffusion coefficient of the mediator. The hematocrit effect interferes with this process because the red blood cells block the diffusion of the mediator to the working electrode. Subsequently, the hematocrit effect influences the amount of current measured at the working electrode without any connection to the amount of glucose in the sample.

Hematocrit bias refers to the difference between the reference glucose concentration obtained with a reference instrument and an experimental glucose reading obtained from a biosensor for samples containing differing hematocrit levels. The difference between the reference and values obtained from the biosensor results from the varying hematocrit levels between specific whole blood samples.

In addition to the hematocrit effect, measurement inaccuracies also may arise when the measurable species concentration does not correlate with the analyte concentration. For example, when a sensor system determines the concentration of a reduced mediator generated in response to the oxidation of an analyte, any reduced mediator not generated by oxidation of the analyte will lead to the sensor system indicating that more analyte is present in the sample than is correct due to mediator background. Thus, "mediator background" is the bias introduced into the measured analyte concentration attributable to measurable species not responsive to the underlying analyte concentration.

In an attempt to overcome one or more of these disadvantages, conventional biosensors have attempted multiple techniques, not only with regard to the mechanical design of the sensor strip and reagent selection, but also regarding the manner in which the measurement device applies the electric potential to the strip. For example, conventional methods of reducing the hematocrit effect for amperometric sensors include the use of filters, as disclosed in U.S. Pat. Nos. 5,708,247 and 5,951,836; reversing the polarity of the applied current, as disclosed in WO 2001/57510; and by methods that maximize the inherent resistance of the sample.

Multiple methods of applying the input signal to the strip, commonly referred to as pulse methods, sequences, or cycles, have been used to address inaccuracies in the determined analyte concentration. For example, in U.S. Pat. No. 4,897,162 the input signal includes a continuous application of rising and falling voltage potentials that are commingled to give a triangular-shaped wave. Furthermore, WO 2004/053476 and U.S. Pat. Docs. 2003/0178322 and 2003/0113933 describe input signals that include the continuous application of rising and falling voltage potentials that also change polarity.

Other conventional methods combine a specific electrode configuration with a input signal adapted to that configuration. For example, U.S. Pat. No. 5,942,102 combines the specific electrode configuration provided by a thin layer cell with a continuous pulse so that the reaction products from the counter electrode arrive at the working electrode. This combination is used to drive the reaction until the current change verses time becomes constant, thus reaching a true steady state condition for the mediator moving between the working and counter electrodes during the potential step. While each of these methods balances various advantages and disadvantages, none are ideal.

As may be seen from the above description, there is an ongoing need for improved biosensors, especially those that may provide an increasingly accurate determination of the analyte concentration in less time. The systems, devices, and methods of the present invention overcome at least one of the disadvantages associated with conventional systems.

SUMMARY

A method for determining the concentration of an analyte in a sample is provided that includes applying an input signal to the sample, the input signal including at least 3 duty cycles within 10 seconds, where each duty cycle includes an excitation pulse and a relaxation. An output signal responsive to a measurable species is measured within 300 milliseconds of applying the excitation pulse of at least one of the duty cycles. The concentration of the analyte in the sample is determined in response to the measured output signal. The duty cycles may each include an excitation at a fixed potential, during which a current may be recorded, and a relaxation. The pulse sequence may include a terminal read pulse and may be applied to a sensor strip including a diffusion barrier layer. The determined analyte concentration may include less bias attributable to mediator background than the same or another method lacking the output signal measurement within 300 milliseconds. Through the use of transient current data, the concentration of the analyte may be determined when a steady-state condition is not reached during the excitation pulses of the duty cycles of the input signal. A data treatment may be applied to the measured currents to determine the concentration of the analyte in the sample.

A handheld measurement device adapted to receive a sensor strip is provided for determining the concentration of an analyte in a sample. The device includes contacts, at least one display, and electronic circuitry establishing electrical communication between the contacts and the display. The circuitry includes an electric charger and a processor, where the processor is in electrical communication with a storage medium. The medium includes computer readable software code, which when executed by the processor, causes the charger to implement an input signal including at least 3 duty cycles within 10 seconds between the contacts. Each duty cycle includes an excitation and a relaxation. The processor is operable to measure at least one current value at the at least two contacts within 300 milliseconds of the charger applying the excitation. The processor also is operable to determine the analyte in the biological fluid in response to the at least one current value.

A biosensor system for determining an analyte concentration in a sample is provided. The system includes a sensor strip having a sample interface adjacent to a reservoir formed by the strip, and a measurement device having a processor connected to a sensor interface. The sensor interface is in electrical communication with the sample interface, and the processor is in electrical communication with a storage medium. The processor determines an output signal value responsive to the concentration of the analyte in the sample from the sensor interface within 300 milliseconds of applying an excitation pulse to the sample interface. The excitation pulse is part of an input signal including at least 3 duty cycles within 10 seconds, each duty cycle including an excitation and a relaxation.

A method of reducing the bias attributable to the hematocrit effect in a determined concentration of an analyte in a sample is provided that includes applying an input signal including at least 3 duty cycles within 10 seconds to the sample. The output signal from which the concentration of the analyte in the sample is determined is recorded within 300 milliseconds of applying an excitation pulse.

BRIEF DESCRIPTION OF THE DRAWINGS

The invention may be better understood with reference to the following drawings and description. The components in the figures are not necessarily to scale, emphasis instead being placed upon illustrating the principles of the invention.

DETAILED DESCRIPTION

In WO 2007/013915, entitled "Gated Amperometry", pulsed input signals are used to analyze analytes in samples. The input signals include alternating excitation and relaxation periods. The present invention relates to a system and method of analyzing the output signals from the pulsed input signals to reduce bias, such as that arising from mediator background and the hematocrit effect. By correlating output signal values measured within 300 ms of the initiation of an excitation pulse, the accuracy and/or precision of the analysis may be improved.

Figure 1:
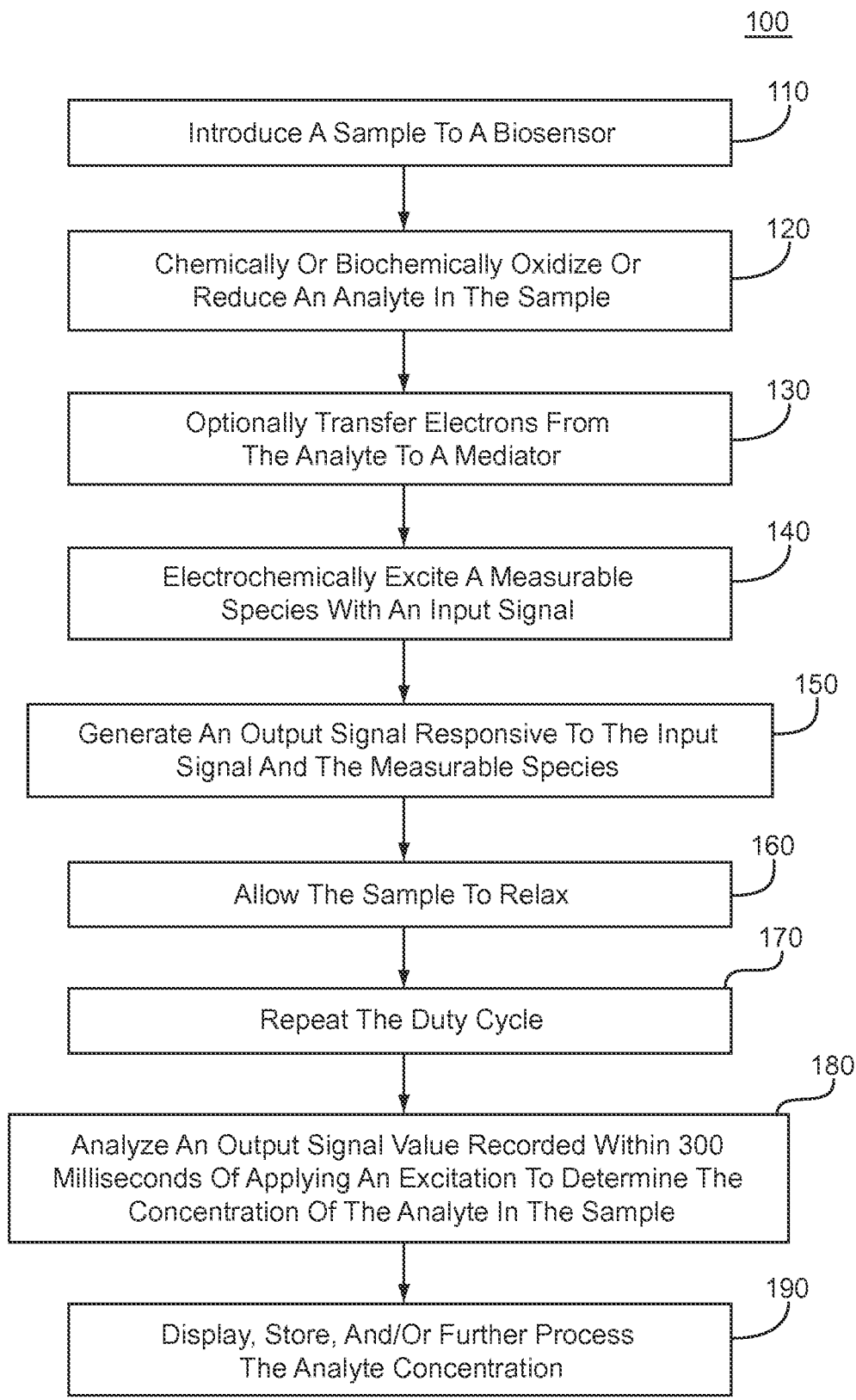
FIG. 1 represents an electrochemical analytic method for determining the presence and/or concentration of an analyte in a sample.

FIG. 1 represents an electrochemical analysis 100 for determining the presence and/or concentration of an analyte in a sample. In 110, the sample is introduced to the biosensor. In 120, a portion of the analyte in the sample undergoes a redox reaction. In 130, electrons are optionally transferred from the analyte to a mediator. In 140, a measurable species is electrochemically excited with an input signal. In 150, an output signal is generated and measured. In 160, the sample is allowed to relax, and in 170, additional excitation pulses are input. In 180, the presence and/or concentration of the sample is determined from the output signal, and in 190, the concentration may be displayed, stored, or the like.

In 110, the sample is introduced to the sensor portion of the biosensor, such as a sensor strip. The sensor strip includes at least one working and at least one counter electrode. The electrodes may include one or more reagent layers. The working electrode may include a diffusion barrier layer that is integral to a reagent layer or that is distinct from the reagent layer. When the working electrode includes a distinct diffusion barrier layer, the reagent layer may or may not be disposed on the diffusion barrier layer.

A diffusion barrier layer provides a porous space having an internal volume where a measurable species may reside. The pores of the diffusion barrier layer may be selected so that the measurable species may diffuse into the diffusion barrier layer, while physically larger sample constituents, such as red blood cells, are substantially excluded. Although conventional sensor strips have used various materials to filter red blood cells from the surface of the working electrode, a diffusion barrier layer provides an internal porous space to contain and isolate a portion of the measurable species from the sample. A more detailed treatment of diffusion barrier layers may be found in U.S. Pub. No. 2007/0246357.

In 120 of FIG. 1, a portion of the analyte present in the sample is chemically or biochemically oxidized or reduced, such as by an oxidoreductase. This occurs as the sample hydrates the reagents. Upon oxidation or reduction, electrons optionally may be transferred between the analyte and a mediator in 130. Thus, an ionized measurable species is formed, such as from the analyte or a mediator. It may be beneficial to provide an initial time delay, or "incubation period," for the reagents to react with the analyte. Preferably, the initial time delay may be from 1 to 10 seconds. A more detailed treatment of initial time delays may be found in U.S. Pat. Nos. 5,620,579 and 5,653,863.

In 140 of FIG. 1, a measurable species, which may be the charged analyte from 120 or the charged mediator from 130, is electrochemically excited (oxidized or reduced) with an input signal. Input signals may be electrical signals, such as current or potential, that pulse or turn on and off at a set sequence. The input signal is a sequence of excitation pulses separated by relaxations. During an amperometric pulse, the electrical potential applied during the excitation is preferably applied at a substantially constant voltage and polarity throughout its duration. This directly contrasts to some conventional excitations where the voltage is changed or "swept" through multiple voltage potentials and/or polarities during data recordation.

During a relaxation of FIG. 1, the electrical signal is off. Off includes time periods when an electrical signal is not present and preferably does not include time periods when an electrical signal is present but has essentially no amplitude. The electrical signal may switch between on and off by closing and opening an electrical circuit, respectively. The electrical circuit may be opened and closed mechanically, electrically, or by other methods.

Input signals may have one or more pulse interval. A pulse interval is the sum of a pulse and the relaxation constituting a duty cycle. Each pulse has an amplitude and a width. The amplitude indicates the intensity of the potential, the current, or the like of the electrical signal. The amplitude may vary or be substantially constant, such as during amperometry, during the pulse. The pulse width is the time duration of the pulse. The pulse widths in an input signal may vary or be substantially the same. Each relaxation has a relaxation width, which is the time duration of the relaxation. The relaxation widths in an input signal may vary or be substantially the same.

By adjusting the width of the excitation and relaxation of the duty cycles, gated input signals may increase the accuracy and/or precision of the analysis. While not wishing to be bound by any particular theory, this increase in accuracy and/or precision may result from drawing the measurable species excited at the working electrode from the interior of a diffusion barrier layer. As opposed to measurable species external to the diffusion barrier layer, which may have a varying rate of diffusion due to red blood cells and other sample constituents, measurable species within the diffusion barrier layer may have a relatively constant diffusion rate to the conductor. For example, and as described in U.S. Pub. No. 2007/0246357, entitled "Concentration Determination in a Diffusion Barrier Layer," a pulse width may be selected to substantially limit measurable species excitation to a diffusion barrier layer.

Preferable input signals include at least 3, 4, 6, 8, or 10 duty cycles applied during less than 30, 10, or 5 seconds. More preferably, at least 3 duty cycles are applied within 10 seconds. Input signals including at least 4 duty cycles applied in less than 7 seconds are especially preferred at present. Preferably, the width of each excitation pulse is independently selected from between 0.1 and 2 seconds and more preferably from between 0.2 and 1 second. At present, especially preferred input signal pulse widths are independently selected from between 0.3 and 0.8 seconds. Preferable pulse intervals are in the range of less than 3, 2.5, or 1.5 seconds. At present, input signals having pulse widths of 0.3 to 0.5 second and pulse intervals from 0.7 to 2 seconds are especially preferred. The input signal may have other pulse widths and intervals.

In 150 of FIG. 1, the biosensor generates an output signal in response to the measurable species and the input signal. The output signal, such as one or more current values, may be measured continuously or intermittently and may be recorded as a function of time. Output signals may include those that decline initially, those that increase and then decline, those that reach a steady-state, and those that are transient. Steady-state currents are observed when the current change with respect to time is substantially constant, such as within ±10 or ±5%. Instead of conventional steady-state or slowly decaying currents, transient (rapidly decaying) current values may be obtained from pulsed input signals.

Figure 2:
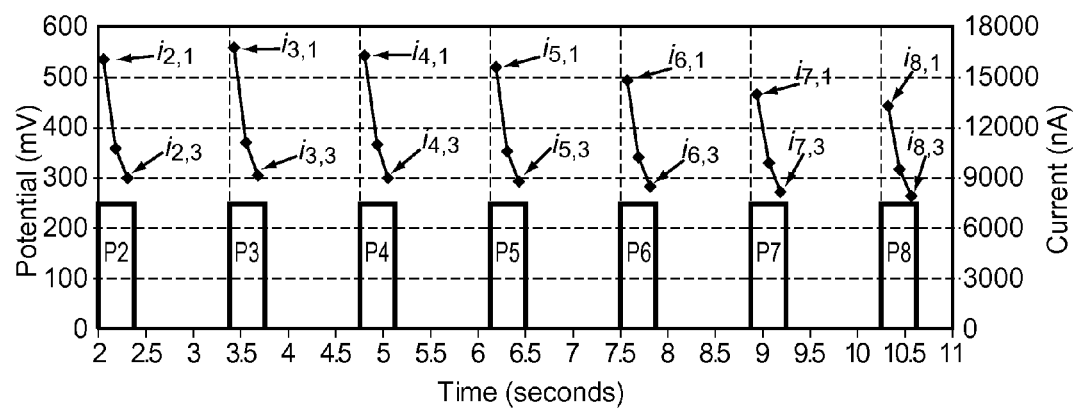
FIG. 2 is a graph illustrating the output signals generated from a gated amperometric input signal.

FIG. 2 is a graph illustrating the output signals generated from a gated amperometric input signal. When plotted as a function of time, each excitation pulse results in a transient decay profile having an initial high current value that decays. The input signal applied by the biosensor included eight pulses and seven relaxations, for a total of seven duty cycles. FIG. 2 omits the first duty cycle and shows that the eighth pulse was not followed by a relaxation. The pulses were applied at about 200 mV and had a pulse width of about 0.4 seconds. The pulse interval for the duty cycles was about 1.4 seconds, providing relaxation widths of about 1 second. The relaxations were provided by an open circuit. While square-wave pulses were used, other wave types compatible with the sensor system and the test sample also may be used.

The biosensor measured the output signal intermittently during each pulse in FIG. 2 and recorded three current values in a memory device. The output signal values were recorded at about 125 millisecond (ms) intervals starting about 125 ms after the initiation of each pulse. The intervals between successive recordings may be the same or different. In FIG. 2, three current values from the output signal were recorded and labeled with the letter I, showing the pulse number and measurement number by subscript. Thus, the third current value measured for the fifth pulse is labeled as $i_{5,3}$.

Figure 3A:
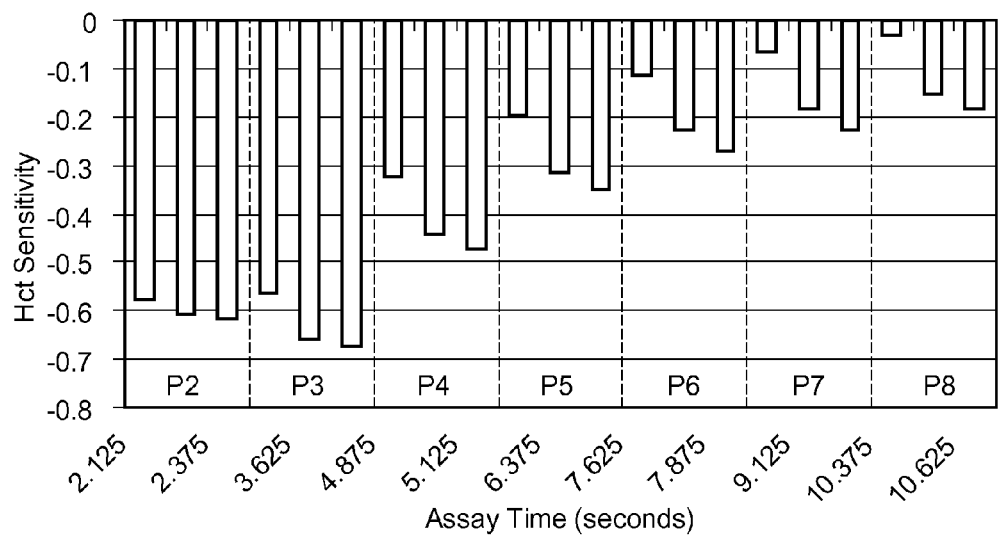
FIG. 3A shows the hematocrit bias present in analyte concentration values determined from each of the three current values measured from each of the seven pulses represented in FIG. 2.

FIG. 3A shows the hematocrit bias present in analyte concentration values determined from each of the three current values measured from each of the seven pulses shown in FIG. 2, with larger hematocrit error represented by larger absolute numerical values on the Y-axis. For each pulse, the first current value showed the least hematocrit bias of the three values, with the bias difference between the first and third values becoming larger with each successive pulse. Lower average hematocrit bias across the measured currents also was observed for each successive pulse; however, each additional pulse prolonged the length of the analysis. Thus, while the current values from P8 included almost no hematocrit error, the first current value from P5 may provide a preferred balance between hematocrit error and analysis time. Also of interest is that the first current value measured for P5 had about the same hematocrit error as the third current value from P8, taken more than 3 seconds later. These results establish that current values measured earlier in the pulse width include the least hematocrit error.

Figure 3B:
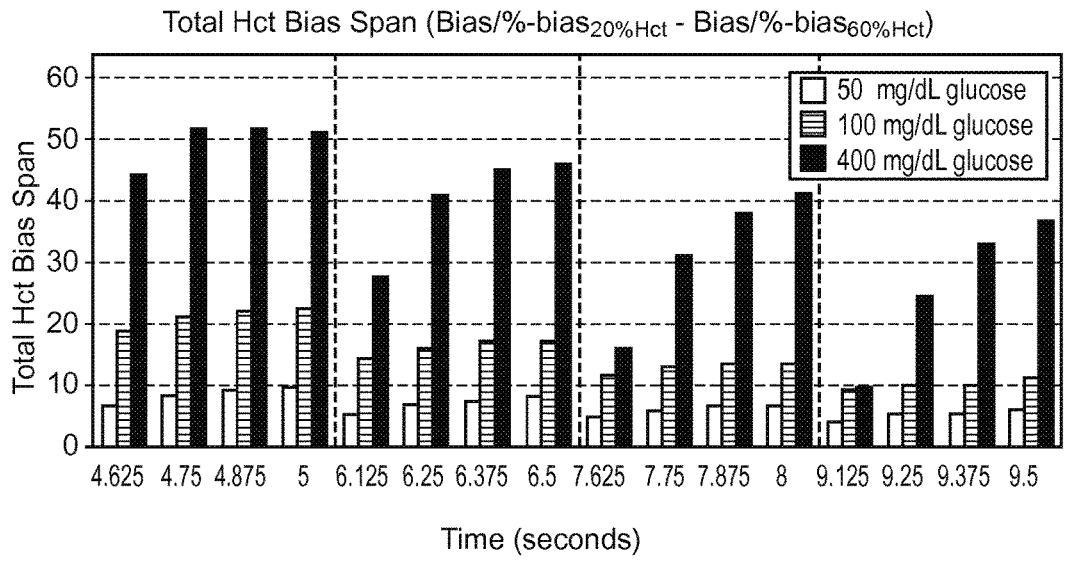
FIG. 3B shows the hematocrit bias span for samples including 50, 100, and 400 mg/dL glucose.

FIG. 3B shows the hematocrit bias span for samples including 50, 100, and 400 mg/dL glucose, with larger span values on the Y-axis representing larger hematocrit error. As in FIG. 3A, the first current value showed the least hematocrit bias of the four current values measured during each pulse, with the bias difference between the first and fourth values becoming larger with each successive pulse. The unexpectedly lower hematocrit bias in the first current value measured for each pulse was more pronounced at the higher 400 mg/dL glucose concentration level. Thus, the accuracy improvement obtained from current measurements taken early in the decay increased as the glucose concentration of the whole blood samples increased.

Figure 4:
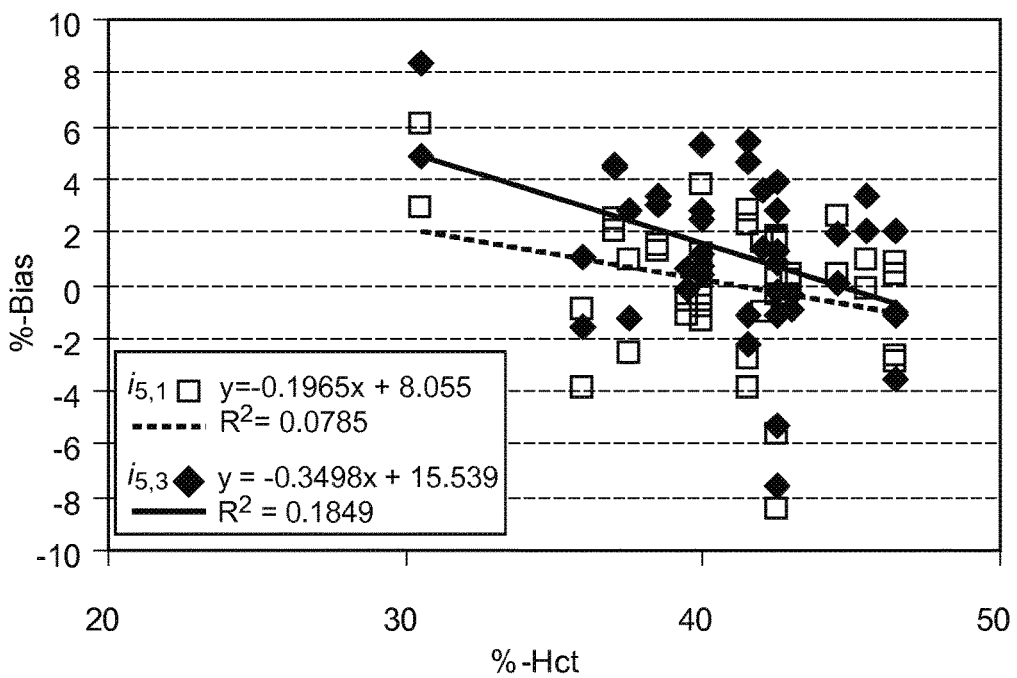
FIG. 4 shows the hematocrit bias for the first and third current values from P5 in FIG. 3A for multiple whole blood samples.

FIG. 4 shows the hematocrit bias for the first and third current values from P5 in FIG. 3A for multiple whole blood samples including varying hematocrit and glucose content. The first current value $i_{5,1}$ showed slope of −0.1965, while the third current value $i_{5,3}$ showed slope of −0.3498, a greater than 40% ((1−0.1965/0.3498)*100) reduction. The improved analyte concentration accuracy obtained from current values taken earlier in the decay is unexpected and directly contrasts with prior teachings that accuracy is achieved from measurements taken in the later steady-state portion of a decay. These results counterintuitively establish that improved accuracy and/or precision may be obtained from measurements taken early in the rapidly changing transient portion of the decay.

Preferably, the output current value from which the analyte concentration is determined is measured within less than 300 ms of applying the excitation pulse. More preferably, the output current value used to determine the analyte concentration of the sample is measured within less than 175 ms from applying an excitation pulse or within 10 to 150 ms of applying the pulse. More preferably still, the output current value from which concentration is determined is measured within 30 to 150 ms of applying an excitation pulse. At present, determining the concentration of the analyte from an output current value measured within 60 to 150 ms of applying an excitation pulse is especially preferred. Preferably, the pulse from which the analytic output current value is measured to determine the concentration of the analyte in the sample is applied within 11 seconds or less of applying the initial excitation pulse and is more preferably applied within 7 seconds or less applying the initial pulse.

In 160 of FIG. 1, the sample undergoes relaxation. The measurement device may open the circuit through the sensor strip, thus allowing relaxation. During the relaxation 160, the current present during the excitation 140 is substantially reduced by at least one-half, preferably by an order of magnitude, and more preferably to zero. Preferably, a zero current state is provided by an open circuit or other method known to those of ordinary skill in the art to provide a substantially zero current flow. Preferably, the output signal is not recorded during the relaxation 160.

During the relaxation 160, an ionizing agent, such as an oxidoreductase, may react with the analyte to generate additional measurable species without the effects of an electric potential. For example, a glucose biosensor including glucose oxidase and a ferricyanide mediator as reagents will produce additional ferrocyanide (reduced mediator) responsive to the analyte concentration of the sample without interference from an electric potential during the relaxation 160.

In 170 of FIG. 1, the biosensor continues to apply pulses from the input signal to the working and counter electrodes for the desired time period. The duty cycle including the excitation 140 and the relaxation 160 may be repeated or a duty cycle having different pulse widths and/or intervals may be applied.

In 180 of FIG. 1, the biosensor analyzes the output signal value recorded within 300 ms of applying a pulse to determine the concentration of the analyte in the sample. Additional current, time, and/or other values also may be analyzed. In 190, the analyte concentration value may be displayed, stored for future reference, and/or used for additional calculations.

Figure 5:
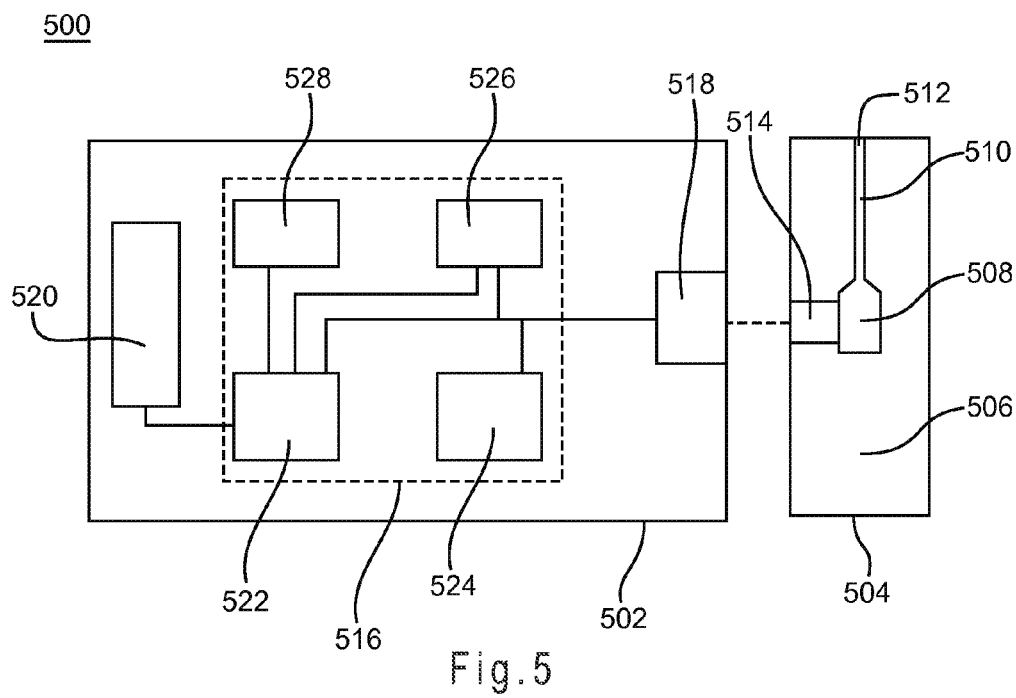
FIG. 5 depicts a schematic representation of a biosensor that determines an analyte concentration in a sample.

FIG. 5 depicts a schematic representation of a biosensor 500 that determines an analyte concentration in a sample of a biological fluid using a pulsed input signal. Biosensor 500 includes a measurement device 502 and a sensor strip 504, which may be implemented in any analytical instrument, including a bench-top device, a portable or hand-held device, or the like. The biosensor 500 may be utilized to determine analyte concentrations, including those of glucose, uric acid, lactate, cholesterol, bilirubin, and the like. While a particular configuration is shown, the biosensor 500 may have other configurations, including those with additional components.

The sensor strip 504 has a base 506 that forms a reservoir 508 and a channel 510 with an opening 512. The reservoir 508 and the channel 510 may be covered by a lid with a vent. The reservoir 508 defines a partially-enclosed volume. The reservoir 508 may contain a composition that assists in retaining a liquid sample such as water-swellable polymers or porous polymer matrices. Reagents may be deposited in the reservoir 508 and/or channel 510. The reagents may include one or more enzymes, binders, mediators, and like species. The sensor strip 504 also may have a sample interface 514 disposed adjacent to the reservoir 508. The sample interface 514 may partially or completely surround the reservoir 508. The sensor strip 504 may have other configurations.

The sample interface 514 has conductors connected to a working electrode and a counter electrode. The electrodes may be substantially in the same plane or in more than one plane. Other separation distances between the electrodes and the lid may be used. The electrodes may be disposed on a surface of the base 506 that forms the reservoir 508. The electrodes may extend or project into the reservoir 508. A dielectric layer may partially cover the conductors and/or the electrodes. The sample interface 514 may have other electrodes and conductors.

The measurement device 502 includes electrical circuitry 516 connected to a sensor interface 518 and a display 520. The electrical circuitry 516 includes a processor 522 connected to a signal generator 524, an optional temperature sensor 526, and a storage medium 528.

The signal generator 524 provides an electrical input signal to the sensor interface 518 in response to the processor 522. The electrical input signal may be transmitted by the sensor interface 518 to the sample interface 514 to apply the electrical input signal to the sample of the biological fluid. The electrical input signal may be a potential or current and may be constant, variable, or a combination thereof, such as when an AC signal is applied with a DC signal offset. The electrical input signal may be applied as a single pulse or in multiple pulses, sequences, or cycles. The signal generator 524 also may record an output signal from the sensor interface as a generator-recorder.

The optional temperature sensor 526 determines the temperature of the sample in the reservoir of the sensor strip 504. The temperature of the sample may be measured, calculated from the output signal, or assumed to be the same or similar to a measurement of the ambient temperature or the temperature of a device implementing the biosensor system. The temperature may be measured using a thermister, thermometer, or other temperature sensing device. Other techniques may be used to determine the sample temperature.

The storage medium 528 may be a magnetic, optical, or semiconductor memory, another storage device, or the like. The storage medium 528 may be a fixed memory device, a removable memory device, such as a memory card, remotely accessed, or the like.

The processor 522 implements the analyte analysis and data treatment using computer readable software code and data stored in the storage medium 528. The processor 522 may start the analyte analysis in response to the presence of the sensor strip 504 at the sensor interface 518, the application of a sample to the sensor strip 504, in response to user input, or the like. The processor 522 directs the signal generator 524 to provide the electrical input signal to the sensor interface 518. The processor 522 may receive the sample temperature from the optional temperature sensor 526. The processor 522 receives the output signal from the sensor interface 518. The output signal is generated in response to the redox reaction of the analyte in the sample. The processor 522 measures the output signal within 300 ms of the application of an excitation pulse from the signal generator 524. The output signal is correlated with the analyte concentration of the sample using one or more correlation equations in the processor 522. The results of the analyte analysis may be output to the display 520 and may be stored in the storage medium 528.

The correlation equations relating analyte concentrations and output signals may be represented graphically, mathematically, a combination thereof, or the like. The correlation equations may be represented by a program number (PNA) table, another look-up table, or the like that is stored in the storage medium 528. Instructions regarding implementation of the analyte analysis may be provided by the computer readable software code stored in the storage medium 528. The code may be object code or any other code describing or controlling the functionality described herein. The data from the analyte analysis may be subjected to one or more data treatments, including the determination of decay rates, K constants, ratios, and the like in the processor 522.

The sensor interface 518 has contacts that connect or electrically communicate with the conductors in the sample interface 514 of the sensor strip 504. The sensor interface 518 transmits the electrical input signal from the signal generator 524 through the contacts to the connectors in the sample interface 514. The sensor interface 518 also transmits the output signal from the sample through the contacts to the processor 522 and/or signal generator 524.

The display 520 may be analog or digital. The display may be an LCD display adapted to displaying a numerical reading.

In use, a liquid sample for analysis is transferred into the reservoir 508 by introducing the liquid to the opening 512. The liquid sample flows through the channel 510, filling the reservoir 508 while expelling the previously contained air. The liquid sample chemically reacts with the reagents deposited in the channel 510 and/or reservoir 508.

The sensor strip 502 is disposed adjacent to the measurement device 502. Adjacent includes positions where the sample interface 514 is in electrical and/or optical communication with the sensor interface 508. Electrical communication includes the transfer of input and/or output signals between contacts in the sensor interface 518 and conductors in the sample interface 514. Optical communication includes the transfer of light between an optical portal in the sample interface 514 and a detector in the sensor interface 518. Optical communication also includes the transfer of light between an optical portal in the sample interface 502 and a light source in the sensor interface 518.

While various embodiments of the invention have been described, it will be apparent to those of ordinary skill in the art that other embodiments and implementations are possible within the scope of the invention. Accordingly, the invention is not to be restricted except in light of the attached claims and their equivalents.

What is claimed is:

1. A method for determining a concentration of an analyte in a sample, comprising:
   receiving the sample at a sample reservoir of a test sensor, the sample including a biological fluid;
   applying, by a signal generator of a measurement device, an electrical input signal to the sample via a sensor interface including at least two electrodes extending or projecting into the sample reservoir, the sample being in electrical communication with the signal generator of the measurement device, wherein the electrical input signal has at least 3 duty cycles within 30 seconds, and wherein each of the at least 3 duty cycles includes an excitation pulse and a relaxation;
   measuring, by a processor of the measurement device via the sensor interface, an electrical output signal responsive to a measurable species within 300 milliseconds from a start of an excitation pulse of at least one of the at least 3 duty cycles, the measurement of the electrical output signal terminating prior to an end of the excitation pulse of the at least one of the at least 3 duty cycles, wherein a pulse width of the excitation pulse of the at least one of the at least 3 duty cycles is from 0.1 to 2 seconds;
   determining, by the processor of the measurement device, the concentration of the analyte in the sample based on the measured electrical output signal; and
   causing to be displayed on a display device an indication of the concentration of the analyte.

2. The method of claim 1, wherein the electrical input signal comprises at least 4 duty cycles within 7 seconds.

3. The method of claim 1, wherein the electrical input signal comprises at least 3 duty cycles within 10 seconds.

4. The method of claim 1, wherein the pulse width of the excitation pulse of the at least one of the at least 3 duty cycles is from 0.3 to 0.8 seconds.

5. The method of claim 1, wherein a pulse interval of the least one of the at least 3 duty cycles is less than 3 seconds.

6. The method of claim 1, wherein the pulse width of the excitation pulse of the at least one of the at least 3 duty cycles is from 0.3 to 0.5 seconds, and wherein a pulse interval of the least one of the at least 3 duty cycles is from 0.7 to 2 seconds.

7. The method of claim 1, wherein the measuring the electrical output signal occurs within less than 175 milliseconds of the excitation pulse of the at least one of the at least 3 duty cycles.

8. The method of claim 1, wherein the measuring the electrical output signal occurs within 60 to 150 milliseconds from the start of the excitation pulse of the at least one of the at least 3 duty cycles.

9. The method of claim 1, further comprising:
transferring at least one electron from the analyte in the sample to a mediator in a sensor strip; and
electrochemically exciting the measurable species in response to the electrical input signal, wherein the measurable species is from at least one of the analyte and the mediator.

10. The method of claim 1, wherein the excitation pulse has a substantially constant voltage.

11. The method of claim 1, wherein the electrical input signal includes square-wave excitations.

12. The method of claim 1, wherein the determining the concentration of the analyte in the sample is carried out with less bias than a concentration of the analyte determined in response to an electrical output signal measured at more than 300 milliseconds from the start of the excitation pulse of one of the duty cycles.

13. The method of claim 12, wherein the determining the concentration of the analyte in the sample is carried out with less bias than a concentration of the analyte determined in response to an electrical input signal having less than 3 duty cycles within 10 seconds.

14. The method of claim 1, further comprising recording at least one current as a function of time during the application of the electrical input signal.

15. The method of claim 1, further comprising applying at least one data treatment to at least one current of the electrical output signal, wherein the at least one data treatment determines at least one of a decay rate, a K constant, and a ratio value.

16. The method of claim 1, further comprising:
exciting the measurable species internal to a diffusion barrier layer; and
substantially excluding from excitation the measurable species external to the diffusion barrier layer.

17. The method of claim 1, wherein the relaxation includes a current reduction to at least one-half of a current flow at an excitation maxima of the excitation pulse.

18. The method of claim 1, wherein the relaxation includes a current flow reduction to at least an order of magnitude less than the current flow at an excitation maxima of the excitation pulse.

19. The method of claim 1, wherein the relaxation includes a substantially zero current flow or an open circuit.

20. The method of claim 19, wherein the relaxation is at least 0.5 seconds.

21. The method of claim 1, wherein the determining the analyte concentration includes determining the analyte concentration from a transient decay, wherein the electrical output signal includes the transient decay.

22. The method of claim 1, wherein the sample is at least one of a biological fluid and a derivative of a biological fluid.

23. The method of claim 1, wherein the electrical input signal comprises a terminal read pulse not followed by a relaxation.

24. The method of claim 1, wherein the measuring the electrical output signal occurs within less than 175 milliseconds from the start of the excitation pulse, wherein the excitation pulse has the pulse width from 0.3 to 0.8 second.

25. The method of claim 1, wherein the measuring the electrical output signal occurs within 60 to 150 milliseconds from the start of the excitation pulse, wherein the excitation pulse has the pulse width from 0.3 to 0.8 second.

26. The method of claim 1, wherein the measuring the electrical output signal occurs within 175 milliseconds from the start of the excitation pulse, and wherein the excitation pulse has a pulse width from 0.2 to 1 second.

27. The method of claim 1, wherein the pulse width of the excitation pulse is greater than 3 seconds and less than or equal to 2 seconds.

28. The method of claim 1, wherein the electrical output signal responsive to the measurable species is measured prior to a termination of the excitation of the at least one of the at least 3 duty cycles.

29. The method of claim 1, wherein the electrical output signal responsive to the measurable species is measured prior to a beginning of the relaxation of the at least one of the at least 3 duty cycles.

30. The method of claim 1, wherein the electrical input signal includes a current or a potential, and wherein the electrical output signal includes a current or a potential.

31. A method for determining a concentration of an analyte in a sample, comprising:
receiving the sample at a sample reservoir of a test sensor, the sample including a biological fluid;
applying, by a signal generator of a measurement device, an electrical input signal to the sample via a sensor interface including at least two electrodes extending or projecting into the sample reservoir, the sample being in electrical communication with the signal generator of the measurement device, wherein the electrical input signal has at least 3 duty cycles within 30 seconds, and wherein each of the at least 3 duty cycles includes an excitation pulse and a relaxation;
measuring, by a processor of the measurement device via the sensor interface, an electrical output signal responsive to a measurable species within 300 milliseconds from the start of an excitation pulse of at least one of the at least 3 duty cycles, the measurement of the electrical output signal terminating while the excitation pulse of the at least one of the at least 3 duty cycles is still being applied to the sample, wherein a pulse width of the excitation pulse of the at least one of the at least 3 duty cycles is from 0.1 to 2 seconds;
determining, by the processor of the measurement device, the concentration of the analyte in the sample based on the measured electrical output signal; and
causing to be displayed on a display device an indication of the concentration of the analyte.

32. The method of claim 31, wherein the electrical input signal includes a current or a potential, and wherein the electrical output signal includes a current or a potential.

33. A handheld measuring device adapted to receive a sensor strip for determining the concentration of an analyte in a sample, the handheld measuring device comprising:
at least two electrodes configured to contact the sample; and
electrical circuitry in electrical communication with the at least two electrodes, the electrical circuitry including a processor in electrical communication with a signal generator and a computer readable storage medium, wherein the processor is programmed to:
cause the signal generator to apply an electrical input signal to the sample, the electrical input signal having at least 3 duty cycles within 30 seconds, each of the at least 3 duty cycles including an excitation pulse and a relaxation;
measure an electrical output signal responsive to a measurable species within 300 milliseconds from a start of an excitation pulse of at least one of the at least 3 duty cycles, the measurement of the electrical output signal terminating prior to an end of the excitation pulse of the at least one of the at least 3 duty cycles, a pulse width of the excitation pulse of the at least one of the at least 3 duty cycles being from 0.1 to 2 seconds; and determine the concentration of the analyte in the sample based on the measured electrical output signal.

34. The handheld measuring device of claim 33, wherein the electrical input signal includes a current or a potential, and wherein the electrical output signal includes a current or a potential.

35. A handheld measuring device adapted to receive a sensor strip for determining the concentration of an analyte in a sample, the handheld measuring device comprising:
   at least two electrodes configured to contact the sample; and
   electrical circuitry in electrical communication with the at least two electrodes, the electrical circuitry including a processor in electrical communication with a signal generator and a computer readable storage medium, wherein the processor is programmed to:
   cause the signal generator to apply an electrical input signal to the sample, the electrical input signal having at least 3 duty cycles within 30 seconds, each of the at least 3 duty cycles including an excitation pulse and a relaxation;
   measure an electrical output signal responsive to a measurable species within 300 milliseconds from a start of an excitation pulse of at least one of the at least 3 duty cycles, the measurement of the electrical output signal terminating while the excitation pulse of the at least one of the at least 3 duty cycles is still being applied to the sample, a pulse width of the excitation pulse of the at least one of the at least 3 duty cycles being from 0.1 to 2 seconds; and
   determine the concentration of the analyte in the sample based on the measured electrical output signal.

36. The handheld measuring device of claim 35, wherein the electrical input signal includes a current or a potential, and wherein the electrical output signal includes a current or a potential.

* * * * *